(12) United States Patent
Mamidipudi et al.

(10) Patent No.: US 10,451,518 B2
(45) Date of Patent: Oct. 22, 2019

(54) ALL FIBER TEMPERATURE AND AIR DENSITY SENSOR

(71) Applicant: RD2, LLC, Manassas, VA (US)

(72) Inventors: Priyavadan Mamidipudi, Great Falls, VA (US); Elizabeth Dakin, Manassas, VA (US); Philip L. Rogers, Hume, VA (US)

(73) Assignee: RD2, LLC, Manassas, VA (US)

( * ) Notice: Subject to any disclaimer, the term of this patent is extended or adjusted under 35 U.S.C. 154(b) by 0 days.

(21) Appl. No.: 15/591,248

(22) Filed: May 10, 2017

(65) Prior Publication Data

US 2017/0328833 A1   Nov. 16, 2017

Related U.S. Application Data

(60) Provisional application No. 62/334,140, filed on May 10, 2016.

(51) Int. Cl.

| G01M 9/00 | (2006.01) |
|---|---|
| G01N 21/00 | (2006.01) |
| G01M 9/06 | (2006.01) |
| G01D 5/353 | (2006.01) |
| G01S 17/95 | (2006.01) |
| G01K 11/32 | (2006.01) |
| G01N 21/65 | (2006.01) |

(52) U.S. Cl.
CPC ........ *G01M 9/065* (2013.01); *G01D 5/35364* (2013.01); *G01K 11/32* (2013.01); *G01N 21/65* (2013.01); *G01S 17/95* (2013.01); *Y02A 90/19* (2018.01)

(58) Field of Classification Search
None
See application file for complete search history.

(56) References Cited

U.S. PATENT DOCUMENTS

| 3,909,132 | A | * | 9/1975 | Barrett | G01J 5/0014 356/301 |
|---|---|---|---|---|---|
| 4,365,153 | A | * | 12/1982 | Seigel | G01N 21/6408 250/253 |
| 5,050,175 | A | * | 9/1991 | Ayral | G02F 1/0338 372/106 |
| 5,153,110 | A | * | 10/1992 | Kawai | G03C 1/035 430/363 |
| RE34,153 | E | * | 12/1992 | Benner | G01N 21/65 356/301 |
| 5,278,402 | A | * | 1/1994 | Wein | G01N 21/41 250/201.9 |
| 5,373,160 | A | * | 12/1994 | Taylor | G01N 21/39 250/338.5 |

(Continued)

*Primary Examiner* — Shawn Decenzo
*Assistant Examiner* — Jarreas C Underwood
(74) *Attorney, Agent, or Firm* — Caesar Rivise, PC

(57) ABSTRACT

Air property measurement (e.g., air temperature, air density, etc.) sensors may take the form of an all-fiber-optic device employing Rotational Raman light detection and ranging technology. Not only do the fiber optic devices described herein require no moving parts, but also these devices may be compact in design and require less power to operate as compared to conventional apparatus. As a result, embodiments may be used in applications in which physical space and power demands may be limited, such as in aircraft.

20 Claims, 4 Drawing Sheets

(56) References Cited

U.S. PATENT DOCUMENTS

| | | | | |
|---|---|---|---|---|
| 5,451,787 A * | 9/1995 | Taylor | | G01N 21/39 250/338.5 |
| 5,504,577 A * | 4/1996 | Lonnqvist | | G01N 21/538 356/342 |
| 5,592,325 A * | 1/1997 | Dodge | | G01J 1/4257 250/338.1 |
| 5,639,162 A * | 6/1997 | Sai | | G01K 11/32 250/227.18 |
| 6,181,412 B1 * | 1/2001 | Popescu | | G01S 17/58 356/28.5 |
| 6,590,911 B1 * | 7/2003 | Spinelli | | H01S 3/108 372/18 |
| 7,116,415 B2 * | 10/2006 | Iuliano | | G01J 3/44 356/301 |
| 7,151,787 B2 * | 12/2006 | Kulp | | G01M 3/38 372/70 |
| 7,180,579 B1 * | 2/2007 | Ludwig | | G01S 7/487 356/4.01 |
| 7,391,506 B2 * | 6/2008 | Harris | | G01S 7/493 356/28.5 |
| 7,463,341 B2 * | 12/2008 | Halldorsson | | G01S 17/95 356/28.5 |
| 7,881,566 B2 * | 2/2011 | Lees | | G01K 11/32 356/51 |
| 8,147,302 B2 * | 4/2012 | Desrochers | | F24F 3/044 454/228 |
| 8,401,608 B2 * | 3/2013 | Baker, Jr. | | A61B 5/0059 600/310 |
| 8,781,755 B2 * | 7/2014 | Wong | | G01S 15/885 702/22 |
| 8,823,938 B2 * | 9/2014 | Beck | | G01N 21/314 356/432 |
| 8,908,160 B2 * | 12/2014 | Dakin | | G01N 21/53 356/28 |
| 9,025,144 B2 * | 5/2015 | Knox | | G01N 15/06 356/338 |
| 9,026,278 B2 * | 5/2015 | Dakin | | G01N 21/53 701/14 |
| 9,086,488 B2 * | 7/2015 | Tchoryk, Jr. | | G01S 17/95 |
| 9,160,137 B1 * | 10/2015 | Abdolvand | | G02F 1/365 |
| 9,372,150 B2 * | 6/2016 | Babin | | G01N 21/255 |
| 9,423,348 B2 * | 8/2016 | Norton | | G01N 15/1459 |
| 9,500,634 B2 * | 11/2016 | Islam | | G01J 3/453 |
| 9,766,262 B2 * | 9/2017 | Smith | | G01P 5/26 |
| 9,863,880 B2 * | 1/2018 | Rothberg | | C12Q 1/6869 |
| 2015/0375342 A1 * | 12/2015 | Gerke | | C03C 23/0025 428/29 |

* cited by examiner

ALL FIBER TEMPERATURE AND AIR DENSITY SENSOR

CROSS REFERENCE TO RELATED APPLICATIONS

This application claims the benefit of U.S. Provisional Application No. 62/334,140, filed May 10, 2016, which is incorporated by reference in its entirety.

STATEMENT REGARDING GOVERNMENT SUPPORT

None.

FIELD

The present disclosure relates to fiber optic sensors and, in particular, fiber optic air temperature and air data sensors.

BACKGROUND

Accurately measuring air properties, including air temperature and air density, can be valuable in numerous applications. For example, these properties can be used in connection with measuring the wind profile (e.g., speed, velocity, and direction) around a moving aircraft. Computing Mach speeds is inaccurate with imprecise air temperature measurement. Likewise, contemporary measurement devices are imprecise aircraft pressure altitude.

While contemporary air property measurement devices are available, they suffer from several limitations, restrictions, and inefficiencies. Simple devices lack precision and can be slow to generate data, particularly where data must be converted and transmitted to other devices for use. Static air pressure ports experience inaccuracies from airflow disturbances caused by air currents and turbulence, icing, and changes in port orientation relative to airflow, such as during changes in aircraft attitude (i.e., the orientation relative to the ground). Complex devices are large, heavy, often involve moving parts, and require considerable power for operation. Such devices are ideal for, given the space, weight, and power constraints of most aircraft.

Furthermore, conventional approaches do not provide reliable systems and methods for making air data measurements at a sample location at a sufficient distance from the aircraft or any physical attachments thereto such that the measurement will not be subject to systemic errors of a sort that cannot always be fully compensated for such as those caused by air compression effects and airflow disturbances.

What is needed is an air property measurement solution with few (if any) moving parts, compact and lightweight in design, and low power requirements, yet still generates highly accurate and real-time data.

BRIEF SUMMARY

Air property measurement (e.g., air temperature, air density, etc.) sensors may take the form of an all-fiber-optic device employing Rotational Raman light detection and ranging technology. Not only do the fiber optic devices described herein require no moving parts, but also these devices may be compact in design and require less power to operate as compared to conventional apparatus. As a result, embodiments may be used in applications in which physical space and power demands may be limited, such as in aircraft. Further, embodiments of the present approach may advantageously provide a more precise computation of Mach speeds, which rely on highly accurate and precise air temperature measurements. Embodiments of the present approach also provide an accurate measurement of temperature and air density that allows for the computation of aircraft pressure altitude accurately and in real time, which alleviates stringent and expensive (both in time and cost) reduced vertical separation minimum (RVSM) requirements.

Embodiments of the present approach may take the form of a fiber optic air property measurement sensor. Fiber optic air property measurement sensors as described herein may have components in fiber optic communication, e.g., connected through fiber optic connectors such as fiber optic cables as are known in the art. Embodiments may include an all-fiber optic laser source configured to emit laser light into air that generates backscattered light. In some embodiments, the laser source may be configured to operate in a master oscillator power amplifier configuration. In some embodiments the laser source further may include an optical modulator configured to modulate light at a rate of about 100 Hz to about 50 kHz. Embodiments of the laser may also include at least one optical fiber amplifier, and in some embodiments the laser source may be down-converted through a non-linear crystal (e.g., lithium triborate crystals) in fiber optic communication with the laser source.

The laser source may be in fiber optic communication with an optical transceiver assembly configured to collect at least a portion of the backscattered light. For example, the laser source may be configured to emit light at a wavelength of about 1064 nm. The optical transceiver assembly may be in fiber optic communication with a receiver to receive the backscattered light along a return signal path and measure backscattered light intensity. Embodiments may feature a return signal path having at least a first optical filter channel and a second optical filter channel, and in some embodiments, each optical filter channel may be configured to filter different spectral portions of the backscattered light to a photoreceiver in fiber optic communication with the optical filter channel. It should be appreciated that embodiments may include one or more computer processing units programmed to measure backscattered light intensity at a photoreceiver, and calculate at least one of air temperature, molecular number density, and air pressure, according to computational methods as are known in the art and described herein.

Optical transceiver assemblies under the present approach may be bistatic or multi-static. Embodiments of the optical transceiver assembly may include a transmitter telescope and at least one receiver telescope, which may be aligned to provide an overlapping field of view at a desired measurement range. In some embodiments, the desired range may be from about 1 m to about 10 m, and more advantageously from about 1 m to about 2 m, from the optical transceiver assembly. Receiver telescopes in some embodiments may include at least one optical bandpass filter configured to pass backscattered light within a desired wavelength into the receiver telescope. In embodiments with multiple receiver telescopes, each receiver telescope may measure backscattered light intensities at a unique wavelength range (e.g., minimal or no overlap in wavelength range between receiver telescopes).

In some embodiments, the fiber optic air property measurement sensor may be housed in a housing telescope. A housing telescope allows for easy transport and installation of the sensor. In some embodiments, however, various components may be housed in separate housing telescopes.

Embodiments having separate housing telescopes may feature fiber optic communication between housing telescopes.

Those of ordinary skill in the art should appreciate that numerous variations may be made to the embodiments disclosed herein without departing from the present approach.

DESCRIPTION

The present approach provides novel techniques and designs for fiber optic air temperature and air density sensors. This disclosure assumes a level of understanding with respect to Rotational Raman light detection and ranging (LIDAR) technology. Some embodiments take the form of all-fiber optic sensors. Some embodiments may be configured for molecular number density measurements. In preferred embodiments, a rotational LIDAR technique is implemented in an all-fiber optic arrangement. Advantageously, the arrangement may have no moving parts.

Figure 1:
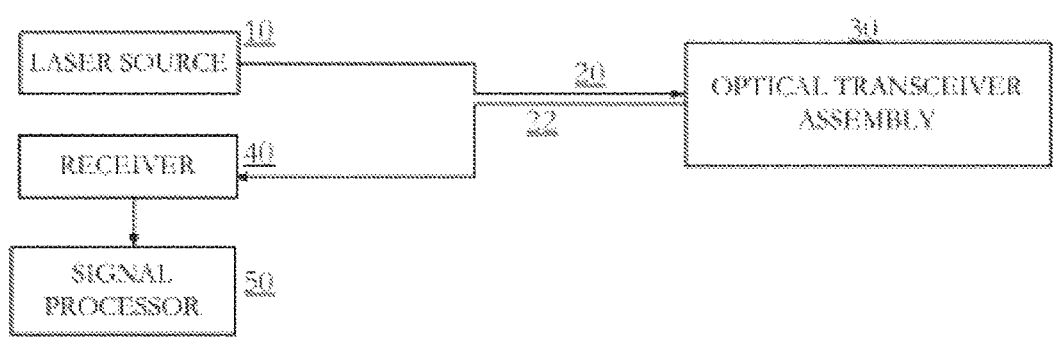
FIG. 1 shows a high level sensor configuration according to some embodiments of the present approach.

FIG. 1 is a diagram showing a high level sensor configuration according to some embodiments. The drawing shows a demonstrative system that may be housed in a telescope (not shown) for convenient installation and mounting. In this configuration, an all-fiber optic laser source 10 is in communication with an optical transceiver assembly 30 through fiber optic cables 20. The optical transceiver assembly 30 is also in communication with a receiver 40 through fiber optic cables 22. The optical transceiver assembly 30 may be remotely located from the laser source 10, and may be bistatic or multi-static depending on the embodiment. In some embodiments, the entire system may be housed in a single housing. In other embodiments, the laser source 10, transceiver assembly 30, and receiver 40 may be housed in separate telescopes, in communication through fiber optic cables as described herein.

During operation, laser source 10 emits light ahead of the system. The emitted laser light interacts with molecules in air (e.g., oxygen and nitrogen). These interactions cause the emitted laser light to scatter. The interaction generates a pure rotational Raman (RR) spectrum within the laser light that is scattered back toward the telescope. The optical transceiver assembly 30 collects a portion of the backscattered light and directs the collected backscattered light to receiver 40. The system may include two or more optical filter channels (not shown) along the return signal path 22. The optical filter channels may be used to extract different spectral portions of the anti-stokes side of the Raman backscatter. The intensity measurement made at the receiver 40 along each of the optical filter channels provides information from which a computer processing unit (not shown) may derive air property measurements, including air temperature, molecular number density, and air pressure. The signal processor 50 may include at least two or more analog-to-digital converters (ADCs) that convert the intensities measured by the receiver assembly 40 into digital voltages for deriving air property measurements.

Figure 2:
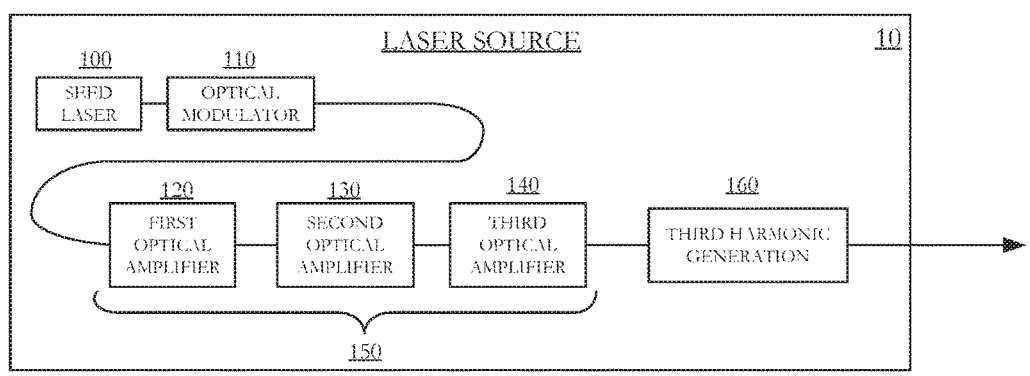
FIG. 2 shows the architecture for a laser source according to some embodiments of the present approach.

FIG. 2 shows the architecture for a laser source 10 according to some embodiments. The laser source 10 in some embodiments operates in a master oscillator power amplifier (MOPA) configuration. A MOPA configuration of the laser source allows scalability in laser output power. In this configuration, seed laser 100 operates at or near a wavelength of about 1064 nm to generate continuous wave laser signals. Optical modulator 110 may modulate these signals at a high rate, such as, for example, between about 100 Hz to about 50 kHz. Laser source 10 may include a series of optical fiber amplifiers 150 to amplify the seed laser signals. The amplifier series 150 in the demonstrative embodiment shown in FIG. 2 includes a first optical amplifier 120, a second optical fiber amplifier 130, and a third optical fiber amplifier 140. It should be appreciated that the number of amplifiers may vary, depending on the measurement distance. Some embodiments may require fewer, if any, whereas some embodiments may require more than three amplifiers. One of ordinary skill in the art may determine the number of amplifiers appropriate for a particular embodiment. The amplified laser signal may be down-converted in wavelength using, for example, a third harmonic generation, through a fiber coupled to a non-linear crystal 160. Non-linear crystal 160 may comprise, for example, lithium triborate crystals.

Figure 3:
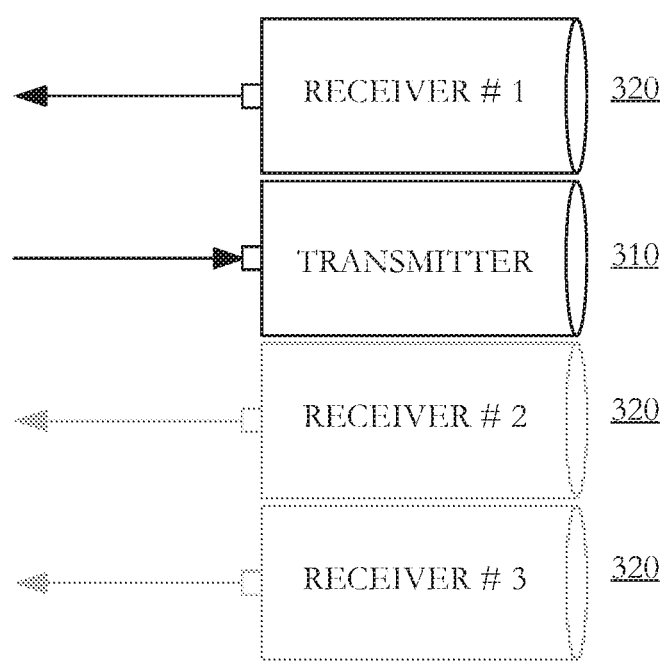
FIG. 3 is a diagram of an optical transceiver assembly according to some embodiment of the present approach.

FIG. 3 is a diagram of an optical transceiver assembly 30 according to an embodiment of the present approach. The optical transceiver assembly 30 may include a transmitter telescope 310 and at least one receiver telescope 320. The transmitter telescope 310 and the receiver telescope 320 may be aligned such that the fields of view overlap at a desired measurement range. The measurement range may be any desired range, and in some embodiments may be from a few meters ahead of the system. Such ranges require less laser power, and require transmitting and receiving angular ranges that allow for compact systems. At closer measurement ranges, transmitting and receiving angles increase, which in turn increases the space between system components and thus the overall size of the system. In some embodiments, the transmitter telescope 310 may be configured to focus the laser signal nominally at a short distance (e.g., about 1 m to about 2 m) away from the telescope. In some embodiments, the transmitter telescope 310 may be configured to collimate the transmitted laser beam.

Each receiver telescope 320 may include one or more optical bandpass filters in the beam path such that only light at the desired wavelengths or within a desired wavelength range passes into the receiver 320. This allows the system to measure intensities at only the wavelengths of consequence, reducing noise and other potentially interfering signals. Additionally, different receiver telescopes 320 may be configured to measure intensities at different wavelength ranges, providing additional data to support various measurement techniques. For example, certain measurement techniques such as described below derive various air properties (e.g., air density) using the ratio of intensities.

Figure 4:
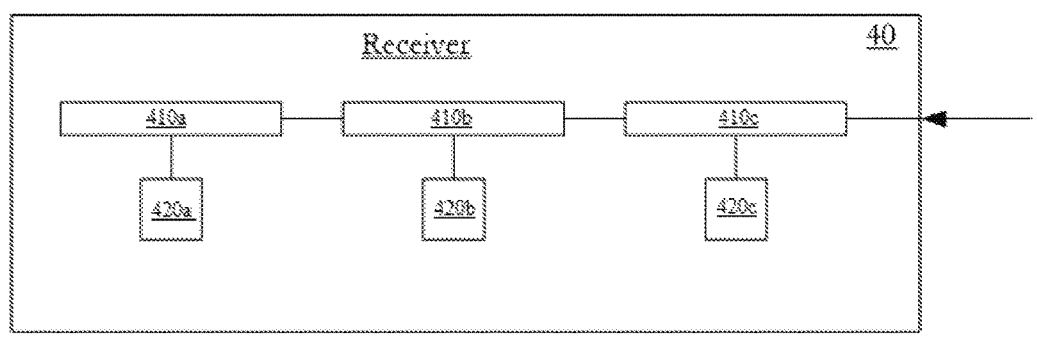
FIG. 4 illustrates a receiver assembly according to some embodiments of the present approach.

FIG. 4 illustrates a receiver assembly 40 according to an embodiment of the present approach. As shown in FIG. 4, receiver assembly 40 may include at least two photoreceivers 420a-420c configured to measure signal intensities of light passing through a corresponding optical filter channel 410a-410c. Each filter channel 410a-410c may be located in the optical transceiver assembly 30. Alternatively, filter channels 410a-410c may be co-located ahead of the photoreceivers 420a-420c within the receiver assembly 40 as shown in FIG. 4. Example photoreceivers include, but are not limited to, PIN, APDs, and PMTs.

Embodiments may be configured to derive various air property measurements from the measured signal intensities at the receiver assembly 40. Embodiments may include one or more computer processing units that may be configured to execute programs for deriving one or more air property measurements. The programs may employ various calculation methods to derive an air property measurement. For example, in embodiments featuring at least two photoreceivers 420a-420c, the intensity ratio of these two pure rotational Raman signals:

$$Q(T, N) = \frac{U_{RR2}(T, N)}{U_{RR1}(T, N)}$$

is a measure of the ambient temperature. In this equation, T is the air temperature and N is the molecular number density.

The calibrated air temperature, $T_{calib}$, may be obtained by calibrating Q with the function:

$$T_{calib} = \frac{-2C'_i}{C'_2 + \sqrt{C'^2_2 - 4C'_1(C'_3 - \ln(Q))}}$$

where $C'_1$, $C'_2$, and $C'_3$ are temperature calibration coefficients.

In the case of molecular number density, the parameter S (T, N) is defined which is directly proportional to the air density:

$$S(N) = (U_{RR1}(T,N) + C_1 U_{RR2}(T,N)) \cdot (1 + C_2 Q(T) + C_3 Q^2(T))$$

where $C_1$, $C_2$, and $C_3$ are obtained via a least square fit in such a way that S varies by less than 0.03% with temperature. Because the rotational Raman spectrum is primarily made up of $O_2$ and $N_2$ lines, contributions from other molecular gases, including water vapor, are almost negligible. However, it should be understood that some embodiments may include corrective factors for such contributions. Effectively, the parameter S is related to the density of dry air, $N_{calib}$, as:

$$N_{CALIB} = \alpha \cdot S$$

where α is a proportionality factor that may be corrected for atmospheric extinction.

It should be appreciated that alternative methods may be used to calculate one or more air property measurements using the measured signal intensities at the receiver assembly 40. The scope of this disclosure is therefore not limited to calculations based on the mathematical relationships described herein.

Embodiments of the present approach may be incorporated into other sensor systems. For example, embodiments of the present approach may be included in systems for detecting aircraft position, such as is disclosed in U.S. Pat. No. 7,898,435, which is incorporated by reference in its entirety. As another example, embodiments of the present approach may be included in optical air data sensory systems, such as those disclosed in U.S. Pat. Nos. 8,508,723 and 8,908,160, which are incorporated by reference in its entirety. As a further example, embodiments of the present approach may be included in laser Doppler velocimeters, such as those disclosed in U.S. Pat. Nos. 5,272,513, 6,141,086, 7,068,355, 7,206,064, 8,508,722, 8,879,051, which are incorporated by reference in their entirety. Embodiments of the present approach may also be included in LIDAR systems, such as those disclosed in U.S. Pat. Nos. 8,930,049 and 9,026,278, which are incorporated by reference in its entirety.

As will be appreciated by one of skill in the art, aspects or portions of the present approach may be embodied as a method, system, and at least in part, on a computer readable medium. Accordingly, the present approach may take the form of combination of hardware and software embodiments (including firmware, resident software, micro-code, etc.) or an embodiment combining software and hardware aspects that may all generally be referred to herein as a "circuit," "module" or "system." For example, measurements and subsequent calculations can be automated, using one or more software modules to characterize the device, record resistance changes, calculate deflections, calculate device temperature, and/or calculate rate of heat accumulation or exchange. Furthermore, the present approach may in part take the form of a computer program product on a computer readable medium having computer-usable program code embodied in the medium. The present approach might also take the form of a combination of such a computer program product with one or more devices, such as a modular sensor, systems relating to communications, control, an integrate remote control component, etc.

Any suitable non-transitory computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the non-transitory computer-readable medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a device accessed via a network, such as the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any non-transitory medium that can contain, store, communicate, propagate, or transport the program for use by or in connection with the instruction execution system, apparatus, or device.

Computer program code for carrying out operations of the present approach may be written in an object oriented programming language such as Java, C++, etc. However, the computer program code for carrying out operations of the present approach may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present approach may be embodied in other specific forms without departing from the spirit or essential characteristics thereof. The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

What is claimed is:

1. An all-fiber optic apparatus for determining air temperature, molecular number density and air pressure on an aircraft in real time using backscattered light, said apparatus comprising:
    a laser source configured to generate laser light in the ultraviolet (UV) spectrum;
    an optical transceiver assembly, coupled to said laser via a fiber optic cable, for emitting said UV laser light into the air, proximate the aircraft, to interact with oxygen and nitrogen molecules, said interaction with oxygen and nitrogen molecules generating backscattered light formed of a pure rotational Raman spectrum, said optical transceiver assembly further comprising at least two receiver telescopes having respective optical filter channels associated therewith for detecting respective spectral portions of an anti-stokes side of said pure rotational Raman spectrum backscattered light;
    at least two photoreceivers, coupled to said optical transceiver assembly via another fiber optic cable, for measuring light intensities of said respective spectral portions; and
    a computer processing unit, coupled to said at least two photoreceivers, configured to calculate at least one of air temperature, molecular number density, and air pressure based on said measured light intensities of said respective spectral portions; and
    wherein said laser source, said optical transceiver assembly and said at least two photoreceivers forming an all-fiber optic configuration.

2. The all-fiber optic apparatus of claim 1, wherein said respective optical filter channels form a portion of said respective receiver telescopes in said optical transceiver assembly.

3. The all-fiber optic apparatus of claim 1, wherein said respective optical filter channels form a portion of said respective photoreceivers.

4. The all-fiber optic apparatus of claim 1, wherein said computer processing unit determines air temperature by forming a ratio of two intensities of said different spectral portions and determines molecular number density by forming a linear combination of said two intensities of said different spectral portions.

5. The all-fiber optic apparatus of claim 1, wherein said laser source comprises at least one optical fiber amplifier.

6. The all-fiber optic apparatus air property measurement sensor of claim 1, wherein said computer processing unit calculates said at least one of air temperature, molecular number density and air pressure in real time.

7. The all-fiber optic apparatus of claim 1, wherein said optical transceiver assembly comprises a transmitter telescope for emitting said UV light into the air.

8. The all-fiber optic apparatus of claim 7, wherein said transmitter telescope and said at least two receiver telescopes are aligned to provide an overlapping field of view at a desired measurement range.

9. The all-fiber optic apparatus of claim 8, wherein the desired range is 1 m to 2 m from said optical transceiver assembly.

10. The all-fiber optic apparatus of claim 1, wherein said optical transceiver assembly is one of bistatic and multistatic.

11. A method for determining air temperature, molecular number density and air pressure on an aircraft in real time using backscattered light detected by an all-fiber apparatus, said method comprising:
    emitting a light in the ultraviolet (UV) spectrum from a laser into the air, proximate the aircraft, to interact with oxygen and nitrogen molecules;
    detecting, using at least one two receiver telescopes, backscattered light from the oxygen and nitrogen molecules that generate a pure rotational Raman spectrum;
    extracting, using respective optical filter channels associated with said at least two receiver telescopes, different spectral portions of an anti-stokes side of said pure rotational Raman spectrum backscattered light; and
    determining temperature, molecular number density and air pressure from intensities of said different spectral portions of an anti-stokes side of said pure rotational Raman spectrum backscattered light.

12. The method of claim 11 wherein said step of determining temperature comprises forming a ratio (Q) of two intensities of said different spectral portions.

13. The method of claim 11 wherein said step of determining molecular number density comprises forming a linear combination of two intensities of said different spectral portions.

14. The method of claim 11 wherein said step of extracting comprises forming said respective optical filter channels within said optical transceiver assembly.

15. The method of claim 11 wherein said step of extracting comprises forming said respective optical filter channels with said respective photoreceivers.

16. The method of claim 11 wherein said step of emitting a light in the UV spectrum from said laser comprises passing said UV spectrum light from said laser into a transmitter telescope that is co-located with said at least two receiver telescopes.

17. The method of claim 11 wherein step of emitting a light in the UV spectrum from said laser comprises passing an initial light wave of said laser source through at least one optical amplifier.

18. The method of claim 16 wherein said step of detecting comprises aligning said transmitter telescope with said at least two receiver telescopes to provide an overlapping field of view at a desired measurement range.

19. The method of claim 18 wherein said desired measurement range is 1 m to 2 m from said transmitter telescope.

20. The method of claim 11 wherein said step of determining temperature, molecular number density and air pressure from intensities of said different spectral portions of an anti-stokes side of said pure rotational Raman spectrum backscattered light is conducted in real time.

* * * * *